United States Patent
Maunoury et al.

(10) Patent No.: US 9,978,946 B2
(45) Date of Patent: May 22, 2018

(54) SPIROBIFLUORENE COMPOUND FOR LIGHT EMITTING DEVICES

(75) Inventors: Jonathan Maunoury, Brussels (BE); Enrico Orselli, Brussels (BE); Dominique Bascour, Grez-Doiceau (BE)

(73) Assignee: SUMITOMO CHEMICAL CO., LTD., Tokyo (JP)

( * ) Notice: Subject to any disclaimer, the term of this patent is extended or adjusted under 35 U.S.C. 154(b) by 965 days.

(21) Appl. No.: 13/878,413

(22) PCT Filed: Oct. 7, 2011

(86) PCT No.: PCT/EP2011/005014
§ 371 (c)(1),
(2), (4) Date: Aug. 16, 2013

(87) PCT Pub. No.: WO2012/048820
PCT Pub. Date: Apr. 19, 2012

(65) Prior Publication Data
US 2013/0327995 A1    Dec. 12, 2013

(30) Foreign Application Priority Data
Oct. 11, 2010   (EP) .................................. 101875159

(51) Int. Cl.
*H01L 51/00* (2006.01)
*C07C 13/72* (2006.01)
(Continued)

(52) U.S. Cl.
CPC .......... *H01L 51/0058* (2013.01); *C07C 13/72* (2013.01); *C07D 209/86* (2013.01);
(Continued)

(58) Field of Classification Search
CPC ................................................ H01L 51/0058
See application file for complete search history.

(56) References Cited

U.S. PATENT DOCUMENTS 8,951,647 B2 *  2/2015  Parham ............... H01L 51/0058
                                                  257/40
2001/0015614 A1   8/2001  Taguchi
(Continued)

FOREIGN PATENT DOCUMENTS

CN    1826841 A    8/2006
CN    1954446 A    4/2007
(Continued)

OTHER PUBLICATIONS

Search Report and Office Action dated Feb. 3, 2017 in TW Application No. 105128113.
(Continued)

*Primary Examiner* — Alex A Rolland
(74) *Attorney, Agent, or Firm* — Panitch Schwarze Belisario & Nadel LLP (57) ABSTRACT

A compound represented by Formula (I) or (II).

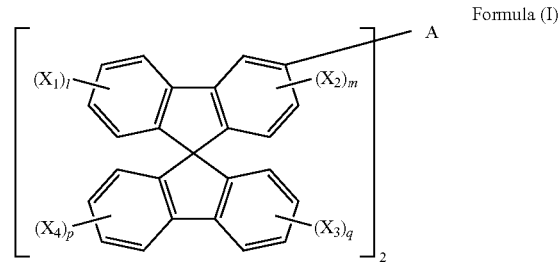

Formula (I)

wherein A is a single bond or a divalent residue of biphenyl, triphenyl, (Continued)

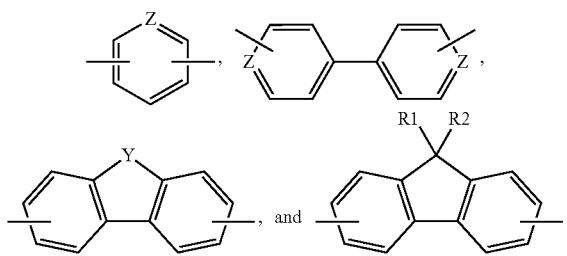

in each of which one or more hydrogen atoms attached in the carbon atoms may be replaced by a substituent other than hydrogen, wherein Z is any one selected from N, O, S, and SiR, Y is N—R, O, S, Si(R)2 where R is $C_{1-20}$ alkyl or aryl, $R^1$ and $R^2$ are independently selected from hydrogen or $C_{1-20}$ alkyl;

X1 to X4 are independently selected from substituents other than spirobifluorenyl, A, $B_1$ or $B_2$ l, p and q are integers of from 0 to 4;

m is an integer of from 0 to 3,

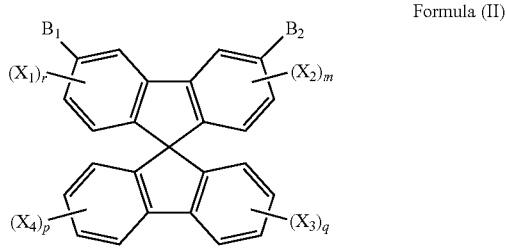

Formula (II)

wherein B1 and B2 are independently selected from hydrogen and a heterocyclic group;

r is an integer of from 0 to 3; and

X1 to X4, m, p, and q are as defined in Formula (I), with the proviso that B1 and B2 are not hydrogen simultaneously.

The use of such compounds in OLEDs is also claimed.

7 Claims, 2 Drawing Sheets (51) Int. Cl.
| | |
|---|---|
| H05B 33/20 | (2006.01) |
| C07D 333/76 | (2006.01) |
| C07D 405/04 | (2006.01) |
| C07D 409/04 | (2006.01) |
| C07D 209/86 | (2006.01) |
| C07D 307/91 | (2006.01) |
| H01L 51/50 | (2006.01) |

(52) U.S. Cl.
CPC ......... *C07D 307/91* (2013.01); *C07D 333/76* (2013.01); *C07D 405/04* (2013.01); *C07D 409/04* (2013.01); *H01L 51/0072* (2013.01); *H01L 51/0073* (2013.01); *H01L 51/0074* (2013.01); *H05B 33/20* (2013.01); *C07C 2603/94* (2017.05); *C09K 2211/185* (2013.01); *H01L 51/5016* (2013.01)

(56) References Cited

U.S. PATENT DOCUMENTS

| | | | |
|---|---|---|---|
| 2003/0168970 A1* | 9/2003 | Tominaga | C07C 15/28 313/504 |
| 2006/0141287 A1 | 6/2006 | Klubek et al. | |
| 2006/0159951 A1 | 7/2006 | Falcou et al. | |
| 2006/0251923 A1* | 11/2006 | Lin | C07F 15/0046 428/690 |
| 2007/0042220 A1 | 2/2007 | Inoue et al. | |
| 2007/0051944 A1* | 3/2007 | Vestweber | C07D 239/26 257/40 |
| 2008/0093980 A1 | 4/2008 | Stoessel et al. | |
| 2008/0166594 A1 | 7/2008 | Ito et al. | |
| 2008/0220286 A1 | 9/2008 | Qiu et al. | |
| 2009/0131673 A1 | 5/2009 | Tanabe et al. | |
| 2010/0066241 A1 | 3/2010 | Cho et al. | |
| 2010/0072887 A1 | 3/2010 | Kwong et al. | |
| 2011/0121274 A1 | 5/2011 | Parham et al. | |
| 2011/0147716 A1* | 6/2011 | Kondakova | H01L 51/5004 257/40 |

FOREIGN PATENT DOCUMENTS

| | | |
|---|---|---|
| CN | 101076508 A | 11/2007 |
| CN | 101143830 A | 3/2008 |
| CN | 101180304 A | 5/2008 |
| CN | 101671291 A | 3/2010 |
| CN | 102712170 A | 10/2012 |
| EP | 2138551 A2 | 12/2009 |
| JP | 2004339136 A | 12/2004 |
| JP | 2006528836 A | 12/2006 |
| JP | 2010027681 A | 2/2010 |
| JP | 2010215759 A | 9/2010 |
| JP | 2013514665 A | 4/2013 |
| WO | 2004016709 A1 | 2/2004 |
| WO | 2006121811 A1 | 11/2006 |
| WO | 2006137210 A1 | 12/2006 |
| WO | WO 2010015306 A1 * 2/2010 ......... H01L 51/0058 |
| WO | 2011075359 A1 | 6/2011 |
| WO | 2012048820 A1 | 4/2012 |

OTHER PUBLICATIONS

Office Action dated Apr. 27, 2015 in CN Application No. 201180059874.9.
Office Action dated Feb. 4, 2014 in EP Application No. 11778793.7.
Office Action dated Nov. 6, 2015 in EP Application No. 11778793.7.
Avilov et al., "Quantum-Chemical Design of Host Materials for Full-Color Triplet Emission," Advanced Materials, vol. 16, No. 18, pp. 1624-1629 (Sep. 16, 2004).
Yang, "Spiro-linked Oligofluorenes and Derivatives: Molecular Design and Theoretical Study of One- and Two-Photon Absorption Properties," Chemical Physics Letters, vol. 461, pp. 9-15 (2008).
Int'l Search Report and Written Opinion dated Jan. 16, 2012 in Int'l Application No. PCT/EP2011/005014.
Extended Search Report dated Jan. 24, 2011 in EP Application No. 10187159.8.
Fournier et al, "Molecular Tectonics. Porous Hydrogen-Bonded Networks Built from Derivatives of 9,9'-Spirobifluorene," Journal of Organic Chemistry, vol. 69, No. 6, pp. 1762-1775 (2004).
Rashidnadimi et al, "Electrochemistry and Electrogenerated Chemiluminescence of 3,6-Di(spirobifluorene)-N-Phenylcarbazole," Journal of the American Chemical Society, vol. 130, No. 2, pp. 634-639 (2008).
Tang et al, "Fluorene Trimers with Various 9,9'-substituents: The Synthesis, Characteristics, Condensed State Structures, and Electroluminescence Properties," Organic Electronics, vol. 9, No. 2, pp. 241-252 (2008).
Office Action dated Jun. 6, 2016 in JP Application No. 2013-533116.
Office Action dated Jun. 1, 2015 in JP Application No. 2013-533116.

(56) References Cited

OTHER PUBLICATIONS

Office Action dated Apr. 21, 2015 in TW Application No. 100136462.
Office Action dated Nov. 29, 2017 in CN Application No. 201610329903.3.
Office Action dated Sep. 20, 2017 in KR Application No. 10-2013-7012167.

* cited by examiner

SPIROBIFLUORENE COMPOUND FOR LIGHT EMITTING DEVICES

TECHNICAL FIELD

The present invention relates to compounds based on spirobifluorene and light emitting devices comprising said compounds.

BACKGROUND ART

Various organic light emitting devices have been under active study and development, particularly those based on electroluminescence (EL) from small organic materials. For such organic devices, the ability to form morphologically stable amorphous films is a key requirement for the development of small materials for organic light emitting diodes (OLEDs). That is because when a small molecule compound is used as the organic light-emitting material, crystallization usually occurs if the molecule of the compound is too small and its structure is too symmetrical. Therefore, when applied in an organic light-emission layer, the small molecule compound is vulnerable to morphological change such as crystallization, and once the crystal is formed, it yields negative impacts upon the light-emitting nature and service life of the OLED.

Thermal stress during device operation can lead to such phase transitions from the amorphous state to the thermodynamically stable polycrystalline state leading to dramatic degradation of the device. As a result it is crucial to design materials featuring high glass transition temperature (Tg>150° C.) in order to stabilize the amorphous state. For improving the stability of devices in order to increase operational lifetime, several host materials have been reported.

Especially, designing materials having a spiro linkage has been a very successful strategy to obtain OLEDs materials with enhanced morphological stability while keeping their electro-optical functionality.

US2006/0141287 discloses light-emitting layers which include a solid organic material containing a mixture of at least two components. The first host component is an organic compound capable of transporting electrical charges and also forms an aggregate. The second component of the mixture is an organic compound capable of transporting electrical charges and, upon mixing with the first host component, is capable of forming a continuous and substantially pin-hole-free layer. In the reference, as the second component, various compounds such as substituted fluorene derivatives, and spirobifluorene derivatives, etc. are used.

US2010/0072887 also discloses light-emitting devices which are made of layers containing organoselenium compounds such as dibenzoselenophene, benzo[b]selenophene, or benzo[c]selenophene derivatives. These organoselenium compounds may serve as hosts for phosphorescent organometallic dopants.

In addition to the above patent references, there are several literature references disclosing spirobifluorene compounds. In Advanced Materials (Weinheim, Germany) (2004), 16(18), 1624-1629, hosts based on oligomers of the carbazole and 9,9'-spirobifluorene (spiro) building blocks, especially para and meta interconnected oligomers, suitable for efficient color-tunable triplet emission, are investigated in terms of the triplet excited-state properties. In this literature reference, the improvement of hole and electron injection in hosts for blue-, green- and red-light emission is also expected for the oligomer. Further, Chemical Physics Letters (2008), 461(1-3), 9-15 also includes simulation results on a series of spiro-linked oligofluorenes and derivatives.

JP 2010/027681 discloses 3,6-Bis-N-carbazolyl-9,9'spirobifluorene.

However, none of the above-disclosed materials meets all the requirements necessary for OLED application, particularly suitable energy level for high phosphorescent efficiency (high triplet energy), high morphological stability, while maintaining other electro-optic and processing properties under operational conditions of the device, such as emission color, dimensional stability, etc. Thus, there has been a need to develop new host materials, which are capable of satisfying all of the requirements indicated above.

SUMMARY OF INVENTION

Surprisingly, it has been found that a spirobifluorene-based compound substituted by an appropriate substituent as defined in the appended claims exhibits both a good lifetime and a good efficiency when it is used in light emitting devices.

In one aspect of the present invention, compounds represented by Formula (I) or (II) are provided as below.

Formula (I)

wherein A is a single bond or a divalent residue of biphenyl, triphenyl, in each of which one or more hydrogen atoms attached in the carbon atoms may be replaced by a substituent other than hydrogen, wherein Z is any one selected from N, O, S, and SiR, Y is N—R, O, S or Si(R)$_2$ where R is C$_{1-20}$ alkyl or aryl, R$^1$ and R$^2$ are independently selected from hydrogen and C$_{1-20}$ alkyl;

X$_1$ to X$_4$ are independently selected from substituents other than spirobifluorenyl;

l, p and q are independently selected from integers of from 0 to 4;
m is an integer of from 0 to 3, Formula (II)

wherein $B_1$ and $B_2$ are independently selected from hydrogen, and a heterocyclic group;
r is an integer of from 0 to 3; and
$X_1$ to $X_4$, m, p, and q are as defined in Formula (I), with the proviso that $B_1$ and $B_2$ are not hydrogen simultaneously with the exception of 3,6-Bis-N-carbazolyl-9,9'-spirobifluorene of the formula The compounds of the present invention can be used in various applications, including in OLED, photovoltaic cells or organic semiconductor devices. For example, those compounds can act as an efficient host material for phosphorescent emitters in OLED. The present invention also provides a device, preferably a light emitting device, comprising said compound.

DESCRIPTION OF EMBODIMENTS

Designing materials having a spiro linkage has been a very successful strategy to obtain OLEDs materials with enhanced morphological stability while keeping their electro-optical functionality. This concept is based on the idea of connecting two molecular π-systems with equal or different functions (emission, charge transport) via a common sp3-hybridized atom. In addition to the spiro linkage, in a compound of the present invention, a substituent is introduced in specific positions to control the triplet energy of the present compound.

The present invention provides a host material, which can be represented by Formula (I) or (II).

Formula (I)

wherein A is a single bond or a divalent residue of biphenyl, triphenyl, and in each of which one or more hydrogen atoms attached in the carbon atoms may be replaced by a substituent other than hydrogen, wherein Z is any one selected from N, O, S, and SiR, Y is N—R, O, S or Si(R)$_2$ where R is C$_{1-20}$ alkyl or aryl, $R^1$ and $R^2$ are independently selected from hydrogen and C$_{1-20}$ alkyl;
$X_1$ to $X_4$ are independently selected from substituents other than spirobifluorenyl,
l, p and q are integers of from 0 to 4;
m is an integer of from 0 to 3, Formula (II)

wherein $B_1$ and $B_2$ are independently selected from hydrogen and a heterocyclic group;
r is an integer of from 0 to 3; and
$X_1$ to $X_4$, m, p, and q are as defined in Formula (I), with the proviso that $B_1$ and $B_2$ are not hydrogen simultaneously, with the exception of 3,6-Bis-N-carbazolyl-9,9'-spirobifluorene of the following formula

Although it is apparent from formula II, it may be expressly mentioned here that X1 to X4 when present (i.e. in those cases where at least one of m, p, q and r is not zero) in compounds of formula II are different from $B_1$ and/or $B_2$.

In some embodiments, the compound is represented by Formula (I) and l, m, p and q are 0. In other embodiments, the compound is represented by Formula (II) and m, r, p and q are 0.

In accordance with the present invention, A, $B_1$ and $B_2$ are substituted in meta position of the spirobifluorene ring since the substitution in the meta position should break the conjugation between the spirobifluorene moieties and the rest of the molecule, ensuring a high triplet energy, and the oligomers of meta-substituted spirobifluorene have higher triplet energy compared to para-substituted ones so that the former is more suitable as hosts for blue emitters. Moreover, the presence of the spiro moieties leads to a high glass transition temperature and promotes the formation of morphologically stable amorphous films, which are essential features for hosts in the OLED emissive layer to produce blue or white light.

In a specific aspect of the invention, A is a single bond. In another aspect, $B_1$ is hydrogen and $B_2$ is a heterocyclic group. The heterocyclic group can be preferably selected from, but is not limited to, carbazole, dibenzothiophene, dibenzofurane, acridine, dibenzosilole, and bipyridine each of which is optionally substituted by one or more substituents other than hydrogen. In one specific embodiment, the heterocyclic group is represented by Formula (III).

Formula (III)

wherein Y is N—R, O, S, Si(R)$_2$ where R is C1-20 alkyl or C1-20 aryl; $X_5$ and $X_6$ are independently selected from substituents other than hydrogen; and s is an integer of from 0 to 3 and t is an integer of from 0 to 4.

In another embodiment, the heterocyclic group is represented by Formula (IV).

(33)

wherein $X_5$ and $X_6$ are independently selected from substituents other than hydrogen; and s and t are independently selected from integers of from 0 to 4.

In more specific embodiments, the compounds of the present invention are represented by any one of Formulae (V) to (VIII).

(V)

(VI)

(VII)

(VIII)

In another specific aspect of the present invention, the compounds are represented by any one of the following formulae IX to XIX

(IX)

(X)

(XI)

(XII)

(XIII)

(XIV)

(XV)

(XVI)

(XVII)

(XVIII)

(XIX)

The synthesis of the compounds of the present invention can be accomplished by any known method. Generally, according to the embodiments of the present invention, the compounds of Formulae (I) and (II) can be prepared by the following reaction schemes:

Scheme 1.

Scheme 2.

-continued wherein X is a leaving group such as halogen, preferably bromine atom.

The present invention is directed to a light emitting device comprising the spirobifluorene compounds of Formula (I) or (II) as above and a light emitting compound. Suitable emitting compounds can be selected from those known in the art and hereafter developed including, without limitation, a metal complex represented by Formula (XX) as disclosed in US 2008/238305:

Formula (XX)

The above mentioned metal complexes, in particular iridium complexes, can exhibit a phosphorescent emission in the visible region of the spectrum. In specific embodiments, the emissive compound exhibits a phosphorescent emission in the blue region of the spectrum.

Another aspect of the present invention relates to an OLED comprising the compound of Formula (I) or (II) and a light emitting compound, specifically a metal complex.

Another aspect of the present invention relates to use of the compound of Formula (I) or (II) and a light emitting compound such as metal complexes as defined above in an OLED.

The OLED device generally comprises:
a glass substrate;
a generally transparent anode such as an indium-tin oxide (ITO) anode;
a hole transporting layer (HTL);
an emissive layer (EML);
an electron transporting layer (ETL); and
a generally metallic cathode such as an Al layer. The emissive layer comprises the host material, and also comprises an emissive material (dopant). The emissive material is adapted to emit light when voltage is applied across the device. The emissive material can be a phosphorescent emitter, more specifically an iridium complex such as those represented by Formula (IX) as above. Those layers are well known in the art, as recited in US 2010/0190984, the disclosures of which are incorporated herein for entirety.

If the emissive material is used as a dopant in a host layer comprising the spirobifluorene compound, then it is generally used in an amount of at least 1 wt %, specifically at least 3 wt %, and more specifically at least 5 wt %, with respect to the total weight of the host and the dopant. Further, it is generally used in an amount of at most 30 wt %, specifically at most 25 wt %.

The present invention also relates to a use of the compounds according to the present invention in OLED, photovoltaic cells or organic semiconductor devices.

EXAMPLES

Hereinafter, the present invention will be explained in detail with reference to examples and comparative examples. These examples, however, should not in any sense be interpreted as limiting the scope of the present invention. Further, units are expressed by weight unless otherwise described.

Synthetic Methods

All reactions were realized under inert atmosphere. The boronic esters used were purchased or synthesized following the usual methods. The solvents and reagents were used as received. All products tested in device were sublimed twice.

Synthetic Example 1

3,6-dibromo-fluorenone

This compound was synthesized following the method of Yong Cao et al. (Advanced Materials. (2008), 20, 2359-2364).

3,6-dibromo-spirobifluorene (3,6-Di-Br-SBF)

Following the method used hereinafter for the formation of 3-bromospirobifluorene, the dibromo compound was isolated with 48% yield.

Compound XVI (XVI)

3 equivalents of the boronic ester of dibenzofurane (17.1 mmol) and 3,6-Di-Br-SBF (5.7 mmol) were solubilized in toluene. The catalyst Pd(PPh$_3$)$_4$, the Na$_2$CO$_3$ and EtOH were then added and the medium was warmed to reflux for 24 h. After evaporation and usual work-up, a white solid was recovered and a flash chromatography afforded the desired product (yield 60%).

Synthetic Examples 2-6

(IX)

(V)

R = S, O or N-tolyl

3-Bromo-fluorenone 3-bromo-spirobifluorene (3-SBF)

In a three ways flask 60 ml of water were added to 8.9 ml of HCl (37% w/w, 2.1 equivalents) and the medium was cooled to 0° C. NaNO$_2$ (1.5 equivalents), dissolved in 50 ml of water, was added dropwise at 0° C. At the end of the addition, 4-amino-2-bromobenzophenone (one equivalent, 15.0 g, 51.6 mmol) solubilized in a mixture of acetone/water (400/230 ml), was added carefully. After 30 minutes at room temperature, the mixture was warmed at 60° C. for 3 hours.

After extraction with methylene chloride and evaporation of the organic phase, a brown solid was recovered (17.4 g) and a flash chromatography was realized. The pure compound was recovered after crystallization with hexane (4.2 g, 32% yield).

This compound was made in two steps from 3-bromo-fluorenone. First, 2-bromobiphenyl (1.05 equivalents, 4.0 g, 16.5 mmol) was solubilized in 102 ml of anhydrous diethyl ether (Et$_2$O). This solution was cooled to −60° C. and BuLi (1.16 eq.) was added dropwise. After 10 min at this temperature, a white precipitate appeared which was redissolved when the medium was warmed to room temperature. 3-bromofluorenone was then added and the reaction mixture was let at 45° C. for one night.

After addition of NH$_4$Cl (5% aq., 260 ml) and extraction with Et$_2$O, 7.0 g of the alcohol was obtained. This solid was solubilized in 141 ml of AcOH and hydrolized by the addition of 78 ml of HCl/dioxane (20 eq.). After evaporation of the solvents, the solid was chromatographied to afford 5.86 g of the target compound (94% yield).

Dispirobifluorene (Compound V)

3-BrSBF (5.3 g, 14.5 mmol) was solubilized in 125 ml of anhydrous THF at RT. Zn (1.54 eq.) and Et$_4$Ni (1 eq) were added to the reaction and the whole mixture was warmed during 2 h to 65° C. NiBr$_2$(PPh$_3$)$_2$ was then added and the medium was warmed to reflux during 72 h. During the reaction, 0.05 equivalents of nickel catalyst could be added. After 48 h the reaction was stopped and the reaction medium was filtered through silica pad. After flash chromatography, the dimer was recovered with 30% yield (m=1.41 g).

3-N-Carbazole-spirobifluorene (Compound IX)

Pd-bis-dibenzylideneacetone Pd(dba)$_2$ (catalyst, 4% mol) and tris-t.-butyl phosphine (P(tBu)$_3$, 0.2 eq) were introduced at room temperature in toluene in a two ways flask. After 15 min under nitrogen, the other reagents (3 Br-SBF (1.9 g, 4.8 mmol), Carbazole (0.84 g, 5.0 mmol) and tBuO Na (1.44 g, 15 mmol)) were introduced and the reaction medium was warmed at 90° C. for 3 hours. After filtration and solvent evaporation, the solid was flash chromatographied to afford 1.7 g of Compound IX (yield 74%, 3.5 mmol).

3-Dibenzothiophene-spirobifluorene (Compound X)

Compound X was prepared in the identical manner as compound XI below except the boronic ester of dibenzothiophene was used instead of that of dibenzofurane (yield 65%).

3-(N-tolyl-carbazole)-spirobifluorene (Compound XIV)

To a flask containing N-tolyl-3-boronic ester carbazole (5.3 mmol, 2.1 eq), 3-Br-SBF (1 eq, 2.5 mmol, 1.0 g) and Pd(PPh$_3$)$_4$ (2% mol, 58 mg), toluene (50 ml), EtOH (10 ml) and 5 equivalents of Na$_2$CO$_3$ aq. 2 M (5 equivalents) was added. After stirring at reflux for 2 days, the reaction was cooled and the product extracted with ether. The organic phases were washed with water and brine. After having been dried over anhydrous MgSO$_4$ and vacuum evaporation of the solvent, the product was recovered by flash chromatography (m=1.4 g, yield 95%).

3-dibenzofurane-spirobifluorene (Compound XI)

(XI)

As for the compound XVI, the boronic ester of dibenzofurane (9.1 mmol) and the 3-Br-SBF (5.7 mmol) were solubilized in toluene. The catalyst Pd(PPh$_3$)$_4$, the Na$_2$CO$_3$ and EtOH were then added and the medium was warmed to reflux for 20 h. After evaporation and usual work-up, 4.5 g of solid was recovered and a chromatography afforded 1.56 g of the pure product (yield 54%).

Characterization of Spirobifluorene Compounds of the Present Invention

All device examples were fabricated by high vacuum thermal evaporation, except for the hole injecting layer, which was deposited by spin-coating technique. The anode electrode was 120 nm of indium tin oxide (ITO). The cathode consisted of 1 nm of LiF followed by 100 nm of Al. All devices were encapsulated with a glass lid sealed with an epoxy resin in a nitrogen glovebox (<1 ppm of H$_2$O and O$_2$) immediately after fabrication, and a moisture getter was incorporated inside the package. The devices were characterized optically and electrically with a C9920-12 External Quantum Efficiency Measurement System from HAMAMATSU. EQE refers to external quantum efficiency expressed in %, PE refers to power efficiency expressed in 1 m/W, while CIE refers to the 1931 Commission Internationale de l'Eclairage (CIE) coordinates. Lifetime tests were done by driving the devices at continuous current at room temperature. LT50 is a measure of lifetime and corresponds to the time for light output to decrease by 50% of the initial value, when the device is driven at a constant current.

Figure 1:
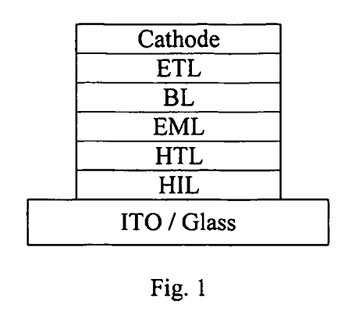
FIG. 1 shows an organic light emitting device having separate electron transport, hole transport, and emissive layers, as well as other layers.
Figure 2:
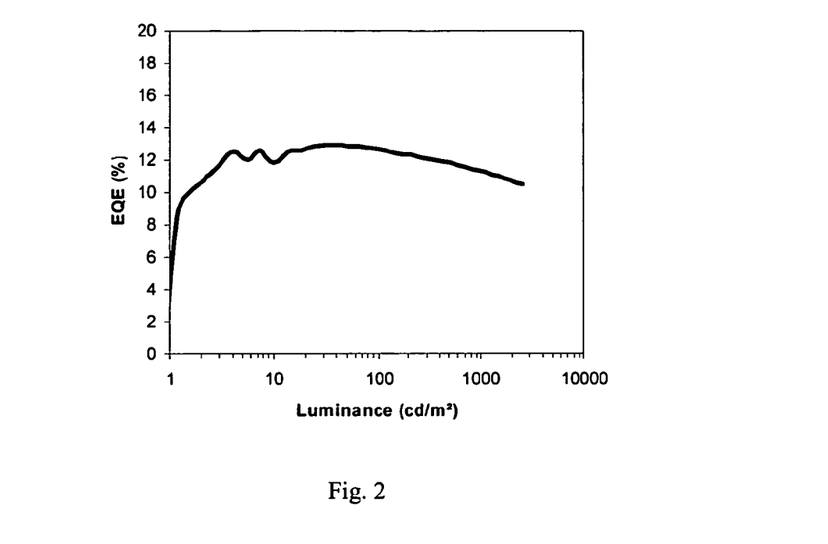
FIG. 2 shows external quantum efficiency versus luminance for the device of Example 2.
Figure 3:
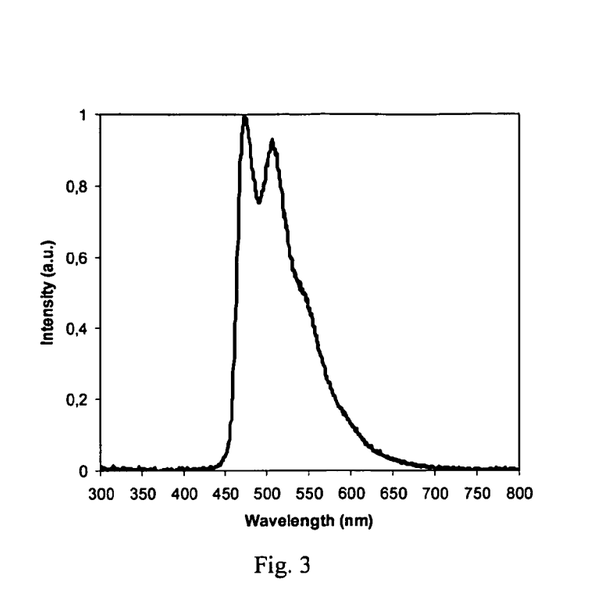
FIG. 3 shows the electroluminescence (EL) spectrum for Example 2.
Figure 4:
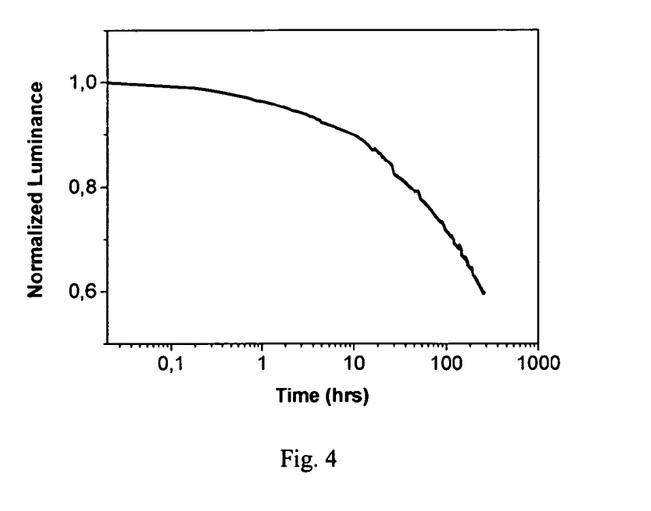
FIG. 4 shows lifetest data (luminescence versus time at $L_0=2000$ Cd/m$^2$) for the device of Example 2.

The organic stack of Examples 1 and 2 consisted of sequentially, from the ITO surface, 60 nm of Plexcore OC AQ-1100 (supplied from Plextronics Inc.) deposited by spin coating and dried on a hot plate at 200° C. for 10 min, 30 nm of N,N'-Bis(naphthalen-1-yl)-N,N'-bis(phenyl)-benzidine (-NPD) as the hole transporting layer (HTL), 30 nm of compound V or compound IX doped with 9, 12.5 or 15% of mc3 (Ir-complex of formula 20) as the emissive layer (EML), 5 nm of 3,3'-di(9H-carbazol-9-yl)biphenyl (mCBP) as the blocking layer (BL), and 40 nm of Bis(2-methyl-8-quinolinolate)-4-(phenylphenolato)aluminium (BAlq) as the electron transporting layer (ETL).

Comparative Examples 1 and 2 were fabricated similarly to Examples 1 and 2, except that DCzT was used as host material and blocking layer in Comparative Example 1, together with Tris(8-hydroxy-quinolinato)aluminium (Alq3) as ETL; while mCBP was used as host material in Comparative Example 2.

The device structures are summarized in Table 1 while Table 2 shows the corresponding measured results for those devices. Percentages are in wt %. As used herein, DCzT, mCBP, compound V and compound IX have the following structures:

DCzT mCBP

Compound V

Compound IX

TABLE 1

| Device | HIL | HTL | Host | Dopant | BL | ETL |
|---|---|---|---|---|---|---|
| Comparative example 1 | Plexcore 60 nm | NPD 30 nm | DCzT | mc3 12.5% | DCzT 5 nm | Alq3 40 nm |
| Comparative example 2 | Plexcore 60 nm | NPD 30 nm | mCBP | mc3 9% | mCBP 5 nm | BAlq 40 nm |
| Example 1 | Plexcore 60 nm | NPD 30 nm | Cpd. V | mc3 15% | mCBP 5 nm | BAlq 40 nm |
| Example 2 | Plexcore 60 nm | NPD 30 nm | Cpd. IX | mc3 15% | mCBP 5 nm | BAlq 40 nm |

As shown in Table 2, the host materials of the invention demonstrated efficiency and lifetime that were better than the comparative examples. In particular, at an initial luminance of 1000 Cd/m$^2$, the results for the lifetimes of the devices show that devices with incorporated the host materials of the present invention had at least a 20% improvement compared to the Comparative Examples.

TABLE 2

| | 1000 cd/m$^2$ | | | |
|---|---|---|---|---|
| Device Example | EQE | PE | CIE (x, y) | LT50 (hrs) |
| Comparative Example 1 | 13.4 | 16.2 | 0.24/0.47 | 1260 |
| Comparative Example 2 | 12.7 | 10.4 | 0.21/0.44 | 1400 |
| Example 1 | 9.3 | 7.5 | 0.22/0.46 | 150 |
| Example 2 | 11.4 | 10.7 | 0.22/0.45 | 1700 |

It will be apparent to those skilled in the art that various modifications and variations can be made to the present invention without departing from the spirit and scope of the invention. Thus, it is intended that the present disclosure covers the modifications and variations of this invention, provided they come within the scope of the appended claims and their equivalents.

The invention claimed is:

1. A compound represented by Formula (II),

Formula (II)

wherein B$_1$ is hydrogen and B$_2$ is a heterocyclic group represented by Formula (III), (III)

wherein Y is O or S; X$_5$ and X$_6$ are independently selected from substituents other than hydrogen; s is an integer of from 0 to 3 and t is an integer of from 0 to 4;

X$_1$ to X$_4$ are independently selected from substituents other than spirobifluorenyl, wherein X$_1$ to X$_4$, if present, are different from B1 and B2;

p and q are integers of from 0 to 4;

m is an integer of from 0 to 3;

and r is an integer of from 0 to 3.

2. A compound in accordance with claim 1, wherein m, r, p and q are 0.

3. A compound in accordance with claim 1, represented by any one of the following formulae:

(X)

(XI)

(XII)

(XIII)

4. A light emitting device comprising a compound of claim 1 and a light emitting compound.

5. The light emitting device of claim 4, wherein the light emitting compound comprises the following compound:

6. An organic light emitting device comprising a compound according to claim 1.

7. An organic light emitting diode comprising a compound according to claim 1.

* * * * *

UNITED STATES PATENT AND TRADEMARK OFFICE
CERTIFICATE OF CORRECTION

PATENT NO. : 9,978,946 B2  
APPLICATION NO. : 13/878413  
DATED : May 22, 2018  
INVENTOR(S) : Jonathan Maunoury et al.

Page 1 of 1

It is certified that error appears in the above-identified patent and that said Letters Patent is hereby corrected as shown below:

On the Title Page

Item (30) Foreign Application Priority Data should read:  
Oct. 11, 2010 (EP)..................101875159.8

Signed and Sealed this  
Fourteenth Day of August, 2018

Andrei Iancu  
*Director of the United States Patent and Trademark Office*